United States Patent [19]

Papenfuhs et al.

[11] Patent Number: 5,902,903
[45] Date of Patent: *May 11, 1999

[54] PROCESS FOR PURIFYING TERTIARY FATTY ALKYLMETHYLAMINES

[75] Inventors: Bernd Papenfuhs, Neuötting; Hubert Seitz, Burgkirchen; Andreas Gallas, Erlbach, all of Germany

[73] Assignee: Hoechst Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/584,169

[22] Filed: Jan. 11, 1996

[30] Foreign Application Priority Data

Jan. 27, 1995 [DE] Germany ............... 195 02 545
Mar. 7, 1995 [DE] Germany ............... 195 07 987

[51] Int. Cl.$^6$ .................................................. C07C 209/84
[52] U.S. Cl. ............................................................ 564/499
[58] Field of Search ................................................ 564/499

[56] References Cited

U.S. PATENT DOCUMENTS

| 2,461,191 | 2/1949 | Babcock | 203/91 |
| 3,441,558 | 4/1969 | Kruger et al. | 536/107 |
| 3,472,740 | 10/1969 | Boothe | 203/37 |
| 4,138,437 | 2/1979 | Strauss et al. | 564/397 |
| 4,845,289 | 7/1989 | Ries et al. | 564/296 |

FOREIGN PATENT DOCUMENTS

| 859665 | 10/1976 | Belgium . |
| 1585480 | 3/1981 | United Kingdom . |

*Primary Examiner*—Jose G. Dees
*Assistant Examiner*—Barbara Badio
*Attorney, Agent, or Firm*—Connolly and Hutz

[57] ABSTRACT

In the process described, purification and improvement in odor of, in particular, fatty alkyldimethylamines is achieved by exposing, in the liquid phase, the tertiary amine to be treated to a vacuum or an inert gas stream. By means of the process according to the invention, in a relatively short time and in a simple and economical manner, a tertiary fatty alkylmethylamine is obtained which is essentially trimethylamine-free and improved in odor.

19 Claims, No Drawings

PROCESS FOR PURIFYING TERTIARY FATTY ALKYLMETHYLAMINES

DESCRIPTION

The invention relates to a process for purifying tertiary fatty alkylmethylamines, in particular fatty alkyldimethylamines, which have been obtained by alkylation of mono- and/or dimethylamine.

Tertiary fatty alkylmethylamines such as difatty alkylmonomethylamine or monofatty alkyldimethylamine (fatty alkyldimethylamine) are known to be advantageously prepared by alkylation of mono- and/or dimethylamine with fatty alcohols or fatty alkyl halides. To work up the reaction product, the catalyst used is filtered off and the tertiary fatty alkylmethylamine is separated off and isolated from high-boiling byproducts by distillation.

Such processes for alkylating mono- and/or dimethylamine are described, for example, in U.S. Pat. No. 4,138,437 and in GB-A-1 585 480. As regards the purity of the isolated tertiary fatty alkylmethylamines, they generally also contain, in addition to unreacted alkylating agent, primary and secondary amines in an amount of in total about<1.5% by weight, based on tertiary fatty alkylmethylamine (compare, for example, U.S. Pat. No. 4,138,437, Example 1).

It has now been shown that tertiary fatty alkylmethylamines of the type described occasionally give off a greater or lesser fish odor, and what is more, virtually independently of the mono- and dimethylamine content.

By careful studies of odorous fatty alkyldimethylamines, it has been found that the substance causing the fish odor may essentially be trimethylamine. The odor threshold of trimethylamine is about 100 to 200 times lower than that of mono- and dimethylamine and the boiling points of the three amines at atmospheric pressure are as follows: monomethylamine −6.32° C., dimethylamine +6.88° C. and trimethylamine +2.87° C.

A process has now been found by which it is possible in a simple and economical manner to separate off trimethylamine from tertiary fatty alkylmethylamines and to obtain simultaneously an improvement in odor.

The process according to the invention comprises exposing, in the liquid phase, the tertiary fatty alkylmethylamine to be purified to a vacuum or an inert gas stream.

Analysis of fatty alkyldimethylamines treated according to the invention unexpectedly shows that they still contain essentially the same amount of mono- and dimethylamine. In view of the boiling points of monomethylamine (−6.32° C.), dimethylamine (6.88° C.) and trimethylamine (2.87° C.), this is indeed a surprising result. It was therefore not to be expected that by the process according to the invention just the trimethylamine content can be reduced and a fatty alkyldimethylamine purified with respect thereto is obtained.

In the process according to the invention, the tertiary fatty alkylmethylamine to be treated is to be present essentially in the liquid state. If, for example, it is inherently liquid at room temperature and atmospheric pressure, further heating is not necessary. In order to ensure the liquid state and a treatment duration as short as possible, the tertiary fatty alkylmethylamine to be purified is generally held at a temperature of 10 to 200° C., preferably 20 to 170° C. Even at said higher temperatures which permit particularly short treatment times, decompositions do not occur. The liquid product is subjected according to the invention to a vacuum, with or without stirring, until the sought-after effect is achieved. The level of the vacuum can be varied within broad ranges and is essentially a function of the time in which it is desired to achieve the purification effect. Thus, short treatment times require a higher vacuum and vice versa. An advantageous vacuum which is applied to liquid product with or without stirring and is maintained is 5 to 500 mbar, preferably 10 to 300 mbar.

The sought-after purification effect is also achieved according to the invention by treating the liquid tertiary fatty alkylmethylamine, with or without stirring, with an inert gas such as nitrogen, argon and/or helium. The inert gas stream used can if appropriate also be air. The amount of inert gas can vary within broad ranges and is likewise essentially a function of the time in which the desired reduction of trimethylamine is to be achieved, in this case also, short treatment times requiring a gas stream higher in amount and velocity and vice versa. An advantageous inert gas stream is 1 l to 300 l, preferably 5 to 200 l, of inert gas per hour and per kilogram of tertiary fatty alkylmethylamine to be treated. It is preferred to pass the inert gas, with or without stirring, through the liquid product, which can be achieved, for example, by a gas tube submerged to a greater or lesser depth in the product. The treatment according to the invention with an inert gas stream for removing trimethylamine is preferably carried out at atmospheric pressure or employing a vacuum, the above-mentioned also applying here with respect to the vacuum level. The inert gas stream treatment can also be carried out when there is a system gage pressure, the inert gas stream having to overcome the system pressure.

Combination of the process according to the invention with other purification steps, such as a distillation, is possible and is not bound to a defined sequence. The process according to the invention represents a simple and economical method for purifying and improving the odor of tertiary fatty alkylmethylamine, independently of the method of preparation of the fatty alkylmethylamine. Both relatively large amounts and only traces of trimethylamine down to below the limit of detection can be removed. The product treated according to the invention generally only contains <1 ppm of trimethylamine. The treatment time in all variants of the process according to the invention is generally in the range from 30 minutes to 10 hours. A further advantage of the process according to the invention is that the secondary products of the purified tertiary fatty alkylmethylamines are also produced with improved odor. Secondary products are, for example, amine oxides and betaines and formulations produced therefrom, for example for the cosmetics sector, cleaning sector, detergent sector and the like.

The tertiary fatty alkylmethylamines to be treated in the context of the present invention are described extensively in the publications mentioned at the outset. They are preferably those of the formula below

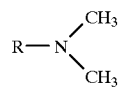

in which R is an alkyl radical or an alkenyl radical having 6 to 24 carbon atoms, preferably 8 to 18 carbon atoms. The alkenyl radical generally contains 1 1 to 3 double bonds. R is frequently also a mixture of alkyl and/or alkenyl radicals, for example $C_{12}$ and $C_{14}$-alkyl ($C_{12/14}$-alkyl), $C_{12}$ and $C_{14}$-alkenyl ($C_{12/14}$-alkenyl) or $C_{12}$ to $C_{18}$-alkyl and/or alkenyl. Examples of alkyl and alkenyl groups are octyl, octenyl, decyl, decenyl, dodecyl (lauryl), dodecenyl, stearyl, oleyl, coconut alkyl and tallow fatty alkyl.

The invention is now described in more detail with reference to examples.

EXAMPLE 1

In Example 1 of U.S. Pat. No. 4 138 437, dimethylamine is reacted with 1-dodecanol in the presence of hydrogen and copper chromite as catalyst. To work up the reaction product, it is filtered off from the catalyst and a dodecyldimethylamine is produced as crude product. The crude product is subjected to vacuum distillation to separate off high-boiling byproducts. The distilled $C_{12}$-alkyldimethylamine obtained after taking off a first runnings contains about 140 ppm of monomethylamine, 150 ppm of dimethylamine and about 64 ppm of trimethylamine and has a more or less unpleasant odor.

200 g of the odorous (distilled) $C_{12}$-alkyldimethylamine are introduced into a reaction vessel equipped with stirrer and thermometer, heated to 40° C. and slowly stirred at this temperature and at a vacuum of 250 mbar. 2 hours after beginning this treatment, the $C_{12}$-alkyldimethylamine is markedly improved in odor. No trimethylamine (TMA) is detectable any longer (detection limit: 1 ppm); monomethylamine (MMA) and dimethylamine (DMA), in contrast, have not been expelled, their content rather has remained virtually constant, as Table 1 below shows:

TABLE 1

| Time [Minutes] | MMA [ppm] | DMA [ppm] | TMA [ppm] |
|---|---|---|---|
| 0 | 140 | 150 | 64 |
| 30 | 140 | 150 | 12 |
| 60 | 139 | 148 | 3 |
| 120 | 138 | 147 | <1 |

EXAMPLE 2

The crude product mentioned in Example 1 contains about 150 ppm of monomethylamine and about 160 ppm of dimethylamine, but 1300 ppm of trimethylamine. In comparison to the distilled dodecyldimethylamine, it has a much more strongly pronounced unpleasant odor. It is subjected to the purification according to the invention.

200 g of the highly odorous crude product $C_{12}$-alkyldimethylamine are introduced into a reaction vessel equipped with stirrer and thermometer, heated to 50° C. and slowly stirred at this temperature and at a vacuum of 50 mbar. After 3 hours, a $C_{12}$-alkyldimethylamine improved in odor is obtained. The original content of 1300 ppm of trimethylamine (TMA) has been reduced to below the detection limit; the content of monomethylamine (MMA) and dimethylamine (DMA), in contrast, has remained virtually unchanged, as Table 2 below shows:

TABLE 2

| Time [Minutes] | MMA [ppm] | DMA [ppm] | TMA [ppm] |
|---|---|---|---|
| 0 | 150 | 160 | 1300 |
| 120 | 145 | 158 | 5 |
| 180 | 143 | 155 | <1 |

EXAMPLE 3

200 g of an odorous $C_{8/10}$-alkyldimethylamine are introduced into a reaction vessel equipped with stirrer, thermometer and gas introduction tube and slowly stirred for 2 hours at 40° C., with a nitrogen stream of 30 l per hour being passed through (the nitrogen introduction tube is placed through the alkyldimethylamine introduced down to the bottom of the reaction vessel). After the 2 hours of treatment according to the invention, the $C_{8/10}$-alkyldimethylamine has the final values, summarized in Table 3 below, of monomethylamine (MMA), dimethylamine (DMA) and trimethylamine (TMA); in Table 3, the initial values are also given:

TABLE 3

| Time [Minutes] | MMA [ppm] | DMA [ppm] | TMA [ppm] |
|---|---|---|---|
| 0 | 70 | 230 | 164 |
| 120 | 69 | 225 | <1 |

EXAMPLE 4

Example 3 is repeated, 200 g of an odorous $C_{16/18}$-alkyldimethylamine being used. In Table 4 below, the initial and final values of the purified amine product are summarized:

TABLE 4

| Time [Minutes] | MMA [ppm] | DMA [ppm] | TMA [ppm] |
|---|---|---|---|
| 0 | 69 | 148 | 14 |
| 120 | 64 | 136 | <1 |

EXAMPLE 5

Example 1 is repeated with the difference that the material is heated to 120° C. instead of 40° C. and is slowly stirred at this temperature and at a vacuum of 250 mbar. Even 1 hour after beginning this treatment, the $C_{12}$-alkyldimethylamine is markedly improved in odor. No trimethylamine (TMA) can be detected any longer (detection limit. 1 ppm); monomethylamine (MMA) and dimethylamine (DMA), in contrast, have not been expelled, their content has rather remained virtually constant, as Table 4 below shows:

TABLE 5

| Time [Minutes] | MMA [ppm] | DMA [ppm] | TMA [ppm] |
|---|---|---|---|
| 0 | 140 | 150 | 64 |
| 60 | 137 | 145 | <1 |

EXAMPLE 6

Example 3 is repeated with the difference that the mixture is slowly stirred for 1 hour (instead of 2 hours) at 80° C. (instead of 40° C.), with a nitrogen stream of 30 l per hour being passed through. Even after treatment for 1 hour, the $C_{8/10}$-alkyldimethylamine has the final values, summarized in Table 6 below, of monomethylamine (MMA), dimethylamine (DMA) and trimethylamine (TMA); the initial values are also given in Table 6:

TABLE 6

| Time [Minutes] | MMA [ppm] | DMA [ppm] | TMA [ppm] |
|---|---|---|---|
| 0 | 70 | 230 | 164 |
| 60 | 67 | 220 | <1 |

EXAMPLE 7

The odorous $C_{16/18}$-alkyldimethylamine mentioned in Example 4 is used and treated in accordance with Example 3 with the difference that it is stirred for 1 hour (instead of 2 hours) at 180° C. (instead of 40° C.), with a nitrogen stream of 30 l per hour being passed through. In Table 7 below, the initial values and final values of the purified amine product are summarized:

TABLE 7

| Time [Minutes] | MMA [ppm] | DMA [ppm] | TMA [ppm] |
|---|---|---|---|
| 0 | 69 | 148 | 14 |
| 50 | 60 | 132 | <1 |

We claim:

1. A process for removing trimethylamine during the preparation of tertiary fatty alkylmethylamines, the process comprising the steps of:

separating a second crude product consisting essentially of tertiary fatty alkylmethylamine, monomethylamine, dimethylamine, and trimethylamine, from a first crude product; and exposing the second crude product to a vacuum, the second crude product being in a liquid state, wherein after said exposing step, the second crude product is essentially free of the trimethylamine.

2. The process of claim 1, wherein said separating step includes separating the second crude product from the first crude product by distillation.

3. The process of claim 2, wherein said separating step includes separating the second crude product from the first crude product by vacuum distillation.

4. The process of claim 1, wherein said exposing step includes exposing the second crude product to a vacuum, the second crude product being in a liquid state and having a temperature of between about 10 and about 200 ° C.

5. The process of claim 4, wherein said exposing step includes exposing the second crude product to a vacuum, the second crude product being in a liquid state and having a temperature of between about 20 and about 170° C.

6. The process of claim 1, wherein said exposing step includes exposing the second crude product to a vacuum of between about 5 and about 500 mbar.

7. The process of claim 1, wherein after said exposing step, the trimethylamine is present in an amount of less than about 1 ppm in the second crude product.

8. The process of claim 1, wherein the tertiary fatty alkylmethylamine is a fatty alkyldimethylamine.

9. The process of claim 1, wherein the first crude product results from the alkylation of alkylamines with a compound selected from fatty alcohols or fatty alkyl halides.

10. A process for removing trimethylamine during the preparation of tertiary fatty alkylmethylamines, the process comprising the steps of:

separating a second crude product consisting essentially of tertiary fatty alkylmethylamine, monomethylamine, dimethylamine, and trimethylamine, from a first crude product; and exposing the second crude product to an inert gas stream, the second crude product being in a liquid state, wherein after said exposing step, the second crude product is essentially free of the trimethylamine.

11. The process of claim 10, wherein said separating step includes separating the second crude product from the first crude product by distillation.

12. The process of claim 11, wherein said separating step includes separating the second crude product from the first crude product by vacuum distillation.

13. The process of claim 10, wherein said exposing step includes exposing the second crude product to the inert gas stream at atmospheric pressure.

14. The process of claim 10, wherein said exposing step includes exposing the second crude product to the inert gas stream at a vacuum of between about 5 and about 500 mbar.

15. The process of claim 10, wherein said exposing step includes exposing the second crude product to the inert gas stream at a gas flow rate of between about 1 and about 300 L/hour.

16. The process of claim 15, wherein said exposing step includes exposing the second crude product to the inert gas stream by passing the inert gas stream through the second crude product.

17. The process of claim 10, wherein after said exposing step, the trimethylamine is present in an amount of less than about 1 ppm in the second crude product.

18. The process of claim 10, wherein the tertiary fatty alkylmethylamine is a fatty alkyldimethylamine.

19. The process of claim 10, wherein the first crude product results from the alkylation of alkylamines with a compound selected from fatty alcohols or fatty alkyl halides.

* * * * *